United States Patent
Heisel (12)

(10) Patent No.: US 6,172,244 B1
(45) Date of Patent: Jan. 9, 2001

(54) METHOD AND REACTOR FOR PRODUCING ETHYLENE OXIDE

(75) Inventor: Michael Heisel, Pullach (DE)

(73) Assignee: Linde Aktiengesellschaft, Hollriegelskreuth (DE)

(*) Notice: Under 35 U.S.C. 154(b), the term of this patent shall be extended for 0 days.

(21) Appl. No.: 09/423,247

(22) PCT Filed: May 6, 1998

(86) PCT No.: PCT/EP98/02673

§ 371 Date: May 24, 2000

§ 102(e) Date: May 24, 2000

(87) PCT Pub. No.: WO98/50375

PCT Pub. Date: Nov. 12, 1998

(30) Foreign Application Priority Data

May 7, 1997 (DE) .............................................. 197 19 375

(51) Int. Cl.[7] .................................................. C07D 301/10
(52) U.S. Cl. ............................. 549/534; 96/299; 261/127
(58) Field of Search .............................. 549/534; 96/299; 261/127

(56) References Cited

U.S. PATENT DOCUMENTS 4,882,444  11/1989  Dobson et al. ....................... 549/534

FOREIGN PATENT DOCUMENTS

| 33 39 570 | 5/1985 | (DE) . |
| 0 081 948 | 6/1983 | (EP) . |
| 0 130 807 | 1/1985 | (EP) . |
| 0 339 748 | 11/1989 | (EP) . |
| 0 529 329 | 3/1993 | (EP) . |
| 0 532 325 | 3/1993 | (EP) . |
| 0 534 195 | 3/1993 | (EP) . |
| 2 161 596 | 1/1986 | (GB) . |

OTHER PUBLICATIONS

Patent Abstracts of JP 07 048305 A (Lion Corp) Feb. 21, 1995.

*Primary Examiner*—Ba K. Trinh
(74) *Attorney, Agent, or Firm*—Millen, White, Zelano & Branigan, P.C.

(57) ABSTRACT

The invention relates to a process for the production of ethylene oxide from a gaseous feedstock—in a cooled exothermic catalytic reaction of ethylene and oxygen from this feed gas in parallel flow-through reaction zones. According to the invention, the reaction zones are limited by cooled dividing walls, and the cooling is achieved by a fluid that flows inside the dividing walls. In addition, the invention relates to a reactor for this purpose with catalyst particles between cooled dividing walls. According to the invention, the cooled dividing walls are formed with the aid of metal plates, and cavities in the form of channels for receiving and for passing through a coolant are arranged for cooling in the metal plates.

10 Claims, 1 Drawing Sheet

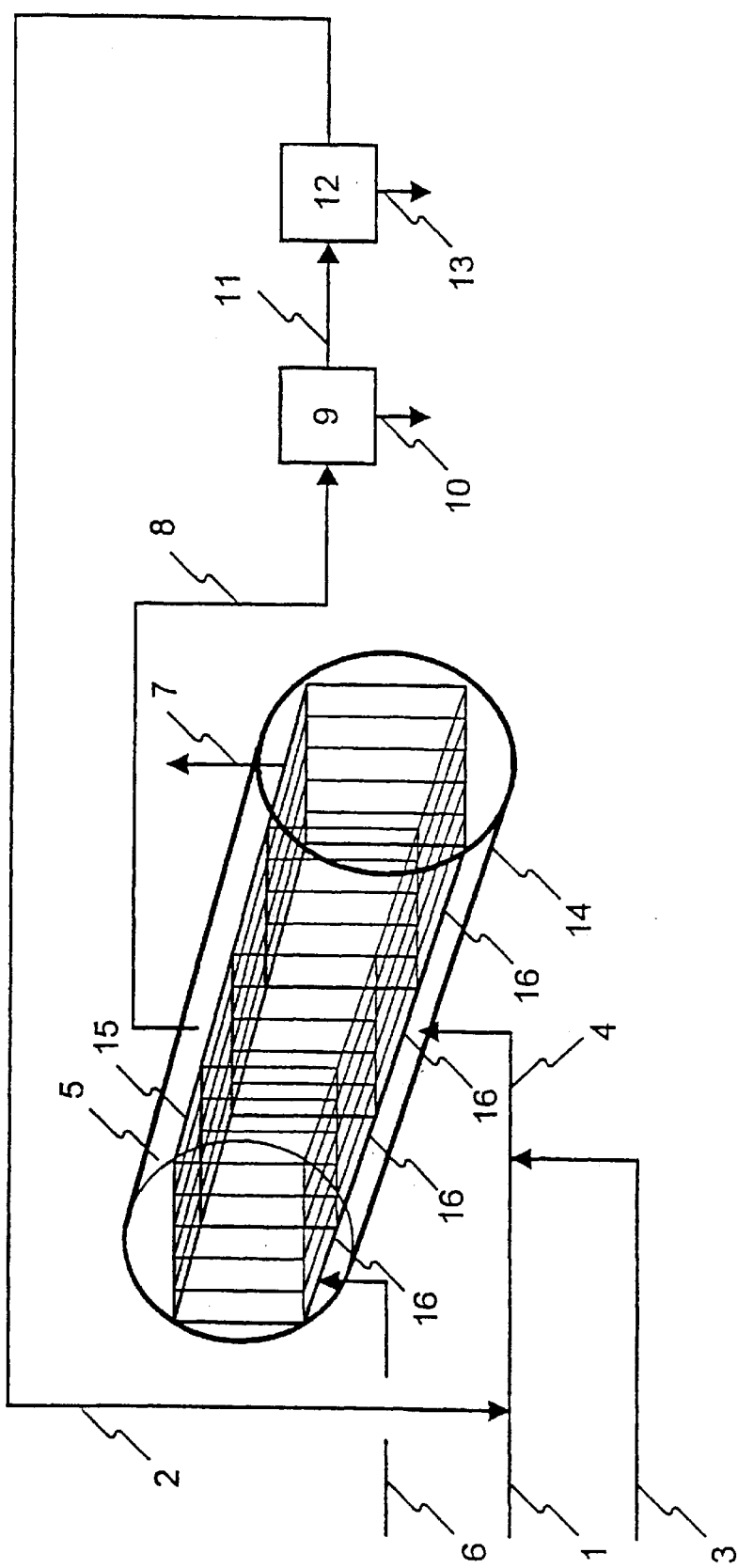

METHOD AND REACTOR FOR PRODUCING ETHYLENE OXIDE

This application is a 371 of PCT/EP98/02673 filed May 6, 1998.

The invention relates to a process for the production of ethylene oxide from a gaseous feedstock—in a cooled exothermic catalytic reaction of ethylene and oxygen from this feed gas in parallel flow-through reaction zones, in addition to a reactor for this process with catalyst particles between cooled dividing walls in at least one reactor container.

Such a process is known from the journal Hydrocarbon Processing, March 1997, page 134. It is used in the tubes in connection with a tubular flow reactor with catalyst particles. The tubes are cooled with boiling water on the shell side of the reactor.

The distribution of the process stream and the catalyst particles in several tubes guarantees that in the case of a malfunction, a self-accelerating reaction caused by local superheating is limited to a reaction tube and does not extend to the entire reactor. This approach and the reactor design also have several drawbacks, however.

- The reactor shell must be designed for the coolant pressure, in practice about 70 bar. As a result, the shell is very thick and thus expensive and heavy to transport, and assembly at the construction site is impossible.
- With a large diameter, the tube sheets are very thick and thus expensive and jeopardized by thermal stress.
- The many reaction tubes can be welded into the thick tube sheets only at great expense.
- The many reaction tubes can be filled only at great expense. In particular, attention must be paid to the same pressure loss in the many different tubes, so that a sparingly loaded reaction tube because of a large pressure drop does not become overheated.
- Because of the high weight, carbon steel is used for the reactor, although rust is thus unavoidable. Rust acts as a catalyst poison, however. When catalyst is emptied, the reactor must therefore be sandblasted, which involves a considerable amount of time spent and financial expense in the majority of the reaction tubes.
- Only stationary reactors are practicable.
- The cooling surface per catalyst volume can be selected only within narrow limits.

The object of the invention is therefore a simple execution of the process in the reactor and a simpler design of the reactor connected to reliable operation in the case of malfunctions and avoidance of the above-mentioned drawbacks.

This object is achieved according to the invention by a process with the features of claim 1 and a reactor with the features of claim 6. Embodiments of the invention are the subject of the subclaims.

A characteristic feature of the invention is that during the process, the reaction zones are formed by cooled dividing walls, and the cooling is achieved by a fluid that flows inside of the dividing walls and that in the reactor, the cooled dividing walls are formed with the aid of metal plates, and cavities in the form of channels for receiving and for passing through a coolant are arranged for cooling in the metal plates.

The separate reaction zones that are implemented by the cooled dividing walls produce a reliable process even in the case of the above-mentioned malfunctions, since superheating of adjacent reaction zones is impossible. The metal plates can be obtained as cooling or heating panels and make possible economical solutions for the reactor internal structures.

In an advantageous embodiment of the process, the gaseous feedstock also contains nitrogen and/or methane in addition to the components ethylene and oxygen. It can thus also be used with oxygen or air that is contaminated with nitrogen. Methane is reproduced with methane that is burned in the feedstock at excessive operating temperatures. This reaction is less exothermic compared to the combustion of ethylene, so that the local superheating is reduced. In addition, the useful substance ethylene remains and can further be fed to the process.

Advantageously, the exhaust gas from the reaction zones with the formed ethylene oxide is subjected to a separation of the ethylene oxide, preferably by a water washing, and thus is obtained as product.

A residual gas that remains after the ethylene oxide is separated can be fed to a $CO_2$ separation, preferably an amine washing, and to a large extent can be reused in the catalytic reaction. This results in a good use of the useful substance ethylene.

Preferably, in the catalytic reaction in the process according to the invention, a space velocity of between 5,000 and 50,000 $h^{-1}$, preferably between 7,000 and 15,000 $h^{-1}$, is used. Because of the low pressure drop in the reactor, it can be selected higher than in the prior art with a maximum of under 5,000 $h^{-1}$. Thus, three advantages are achieved:

1. The high space velocities result in better selectivity of the catalyst and thus make possible a better degree of use of the ethylene used, i.e., increases the economic efficiency of the process.

2. Better selectivity means that the undesirable secondary reaction of the complete combustion of ethylene into $CO_2$ and water is better suppressed. This secondary reaction is very strongly exothermic, i.e., releases a lot of heat. When this reaction occurs, the temperature consequently increases. When the temperature increases, the selectivity of the catalyst worsens, so that the undesirable secondary reaction is amplified. This can progress to the point where the catalyst and/or the reactor are irreversibly damaged. The process according to the invention improves the selectivity and thus increases the reliability of the production of ethylene oxide.

3. The catalyst volume, which is necessary for the conversion of a certain amount of crude gas, is smaller. The entire reactor thus can be smaller and consequently less expensive. Since less of the reactive gas is then contained in the reactor, safety is further increased by this effect.

In an advantageous embodiment of the reactor according to the invention, several metal plates, preferably vertical and some distance apart, are joined to form a packet of metal plates and thus form a free space, into which the catalyst particles are poured. Tube sheets are no longer necessary, and the reaction spaces between the plates can be filled in a way that is similar to a fixed bed without cooling. This is a significant improvement compared to a reactor according to the prior art.

The metal plate packets are advantageously formed from flat plates that are preferably parallel and from cylindrically curved, preferably concentric plates. Such plates, also plate packets, are economical and commercially available.

In a preferred embodiment of the reactor according to the invention, several metal plate packets are arranged beside one another in the reactor container, such that they form a module of plate packets, in which the feed gas flows in a parallel manner through the plate packets. This is easy to implement, especially in horizontal containers, without encountering structural limits, and small pressure drops are made possible in the process.

Several modules can also be arranged either in the same reactor container, preferably on top of one another, or in several reactor containers through which feed gas flows in succession. Together with the option of selecting between upright and horizontal reactor containers, the reactor can be matched optimally to the available space and the permissible pressure drop in the reactor.

Further advantages of the process according to the invention will emerge from the interaction of the features of the invention with those of their advantageous embodiments:

The reactor shell must tolerate only the gas pressure, not the higher pressure of the steam, which is produced during cooling.

The reactor is significantly lighter than a reactor according to the prior art and can be built from high-grade steel, so that the problems of carbon steel are avoided.

The cooling surface per catalyst volume can be freely selected within very wide limits.

Since the reactors according to the invention are significantly lighter with the same output, shipping, assembly and foundation work are less expensive than in reactors according to the prior art.

Design limits and safety concerns do not limit the installable production capacity at a site.

The invention is explained in more detail with a FIGURE based on an embodiment.

The FIGURE diagrammatically shows an embodiment of the process according to the invention with the reactor according to the invention.

Ethylene 1 and recycle gas 2 from a rear part of the plant are mixed with oxygen 3 in a feedstock 4 and fed to a reactor 5, which is cooled with boiler feedwater 6, so that in this case, vapor 7 accumulates. Ethylene oxide 10 is separated from exhaust gas 8 from reactor 5 in a water washing 9, and residual gas 11 with the by-product $Co_2$ that is produced in reactor 5 is fed to an amine washing 12, in which $CO_2$ 13 is separated. After additional purification steps, which are not depicted in the FIGURE, the residual gas from which in particular $CO_2$ has been removed is reused as recycle gas 2 completely or partially in feedstock 4 of the reactor.

In addition, the FIGURE diagrammatically shows reactor 5 as a horizontal container 14, in which a module 15 that consists of plate packets 16 is arranged. It is indicated that packets 16 consist of cooled, parallel plates, whose edges in the FIGURE are depicted as lines. In their design, the cooled plates can resemble heating units for housing and office spaces. The catalyst beds between the plates are not depicted in the FIGURE.

A typical use of the process according to the invention with the reactor according to the invention contains approximately 30% ethylene, 60% methane, 5% oxygen and 5% nitrogen and water vapor.

What is claimed is:

1. Process for the production of ethylene oxide from a gaseous feedstock—in a cooled, exothermic, catalytic reaction of ethylene and oxygen from this feed gas in parallel flow-through reaction zones, characterized in that the reaction zones are limited by cooled dividing walls, and the cooling is achieved by a fluid that flows inside the dividing walls.

2. Process according to claim 1, wherein the gaseous feedstock also contains nitrogen and/or methane in addition to the components ethylene and oxygen.

3. Process according to claim 1, wherein the exhaust gas from the reaction zones with the ethylene oxide that is formed is subjected to a separation of the ethylene oxide, preferably by a water washing.

4. Process according to claim 1, wherein a residual gas that remains after the ethylene oxide is separated is fed to a $CO_2$ separation, preferably an amine washing, and wherein the residual gas that is largely released from $CO_2$ is at least partially recycled, the feedstock is mixed in and is reused in the catalytic reaction.

5. Process according to claim 1, wherein in the catalytic reaction, a space velocity of between 5,000 and 50,000 $h^{-1}$, preferably between 7,000 and 15,000 $h^{-1}$, is used.

6. Reactor for the production of ethylene oxide according to claim 1 with catalyst particles between cooled dividing walls in at least one reactor container, wherein the cooled dividing walls are formed with the aid of metal plates, and a coolant is used for cooling cavities in the metal plates in the form of channels for receiving and for passing through.

7. Reactor according to claim 6, wherein in each case several metal plates, preferably vertical and some distance apart, are joined to form a packet of metal plates and thus form a free space, in which the catalyst particles are poured.

8. Reactor according to claim 7, wherein the metal plate packets are formed from flat, preferably parallel plates or from curved plates that are preferably arranged as a concentric cylinder.

9. Reactor according to claim 7, wherein several metal plate packets are arranged beside one another in the reactor container, such that they form a module of plate packets in which the feed gas flows in a parallel manner through the plate packets.

10. Reactor according to claim 9, wherein feed gas flows through several modules either in the same reactor container, preferably on top of one another, or in succession in several reactor containers.

* * * * *